(12) United States Patent
Ferrero Lindlau

(10) Patent No.: US 12,186,259 B2
(45) Date of Patent: Jan. 7, 2025

(54) DEVICE FOR CARDIO-PULMONARY RESUSCITATION OF A PATIENT

(71) Applicant: DISEÑO Y PRODUCCIÓN DE SISTEMAS RCP S.L., Gurrea de Gallego (ES)

(72) Inventor: Adolfo Ferrero Lindlau, El Temple (ES)

(73) Assignee: DISEÑO Y PRODUCCIÓN DE SISTEMAS RCP S.L., Gurrea de Gallego (ES)

( * ) Notice: Subject to any disclaimer, the term of this patent is extended or adjusted under 35 U.S.C. 154(b) by 591 days.

(21) Appl. No.: 17/621,355

(22) PCT Filed: Jul. 13, 2020

(86) PCT No.: PCT/ES2020/070454
§ 371 (c)(1),
(2) Date: Dec. 21, 2021

(87) PCT Pub. No.: WO2021/009403
PCT Pub. Date: Jan. 21, 2021

(65) Prior Publication Data
US 2022/0362101 A1 Nov. 17, 2022

(30) Foreign Application Priority Data
Jul. 15, 2019 (ES) .............................. ES201931210U

(51) Int. Cl.
*A61H 31/00* (2006.01)
*A61G 13/12* (2006.01)
*A62B 7/02* (2006.01)

(52) U.S. Cl.
CPC ......... *A61H 31/004* (2013.01); *A61G 13/121* (2013.01); *A61G 13/1235* (2013.01); *A61H 31/008* (2013.01); *A62B 7/02* (2013.01)

(58) Field of Classification Search
None
See application file for complete search history.

(56) References Cited

U.S. PATENT DOCUMENTS 2,566,351 A * 9/1951 Meuler ................ A61H 31/008
968/805
2,637,318 A * 5/1953 Emerson .............. A61H 31/008
601/41

(Continued)

FOREIGN PATENT DOCUMENTS

WO  2017/066770 A1  4/2017
WO  2018/129024 A1  7/2018

OTHER PUBLICATIONS

International Search Report of PCT/ES2020/070454, mailed Oct. 2, 2020.

*Primary Examiner* — LaToya M Louis
(74) *Attorney, Agent, or Firm* — Collard & Roe, P.C.

(57) ABSTRACT

A device for cardio-pulmonary resuscitation of a patient includes a support base, a swivel support, a mask holder and two lateral support elements. The support base is wedge-shaped in order to support the patient. There are guiding means and swivel elements provided in the support base and in the swivel support. The device makes it possible to adjust the position of the mask holder both vertically and horizontally to adapt to the dimensions of the user via a plurality of toothed elements. The configuration allows the combination with any existing continuous ventilation equipment.

10 Claims, 6 Drawing Sheets

(56) References Cited

U.S. PATENT DOCUMENTS

| | | | | |
|---|---|---|---|---|
| 2,660,495 A * | 11/1953 | Schwalbe | A61H 31/008 | 5/624 |
| 2,702,546 A * | 2/1955 | Gilroy | A61G 10/04 | 135/96 |
| 2,742,040 A * | 4/1956 | Moore | A61G 10/04 | 62/304 |
| 2,963,247 A * | 12/1960 | Collier | A61M 16/0672 | 604/23 |
| 3,461,858 A | 8/1969 | Michelson | | |
| 3,464,411 A * | 9/1969 | Martinez | A61M 16/06 | 128/207.14 |
| 3,506,003 A * | 4/1970 | Gregory | A61M 16/16 | 128/203.29 |
| 4,196,725 A | 4/1980 | Gunderson | | |
| 4,266,759 A * | 5/1981 | Liebman | A61H 31/008 | 5/632 |
| 4,297,999 A | 11/1981 | Kitrell | | |
| 4,534,075 A * | 8/1985 | Schnitzler | A61G 1/0231 | 5/628 |
| 4,615,058 A * | 10/1986 | Feldt | A61G 13/00 | D12/132 |
| 4,915,095 A * | 4/1990 | Chun | A61H 31/008 | 601/43 |
| 5,038,757 A * | 8/1991 | Yamasaki | A61G 7/05 | 601/102 |
| 6,224,027 B1 * | 5/2001 | Johnson | A61M 5/1415 | 248/129 |
| 6,446,288 B1 * | 9/2002 | Pi | A61G 7/072 | 5/636 |
| 6,691,347 B2 * | 2/2004 | Hand | A61B 6/0487 | 5/607 |
| 6,817,363 B2 * | 11/2004 | Biondo | A61H 9/0078 | 5/607 |
| 6,935,340 B2 * | 8/2005 | Saied | A61M 16/0488 | 128/845 |
| 7,040,581 B2 * | 5/2006 | Noelke | A61G 7/0503 | 5/503.1 |
| 7,108,326 B2 * | 9/2006 | Schurg | B64D 11/0638 | 297/343 |
| 7,513,252 B2 * | 4/2009 | Berg | A61M 16/009 | 128/205.12 |
| 7,931,021 B2 * | 4/2011 | Livingston | A61M 16/06 | 128/206.24 |
| 8,535,251 B1 * | 9/2013 | Rao | A61H 31/007 | 601/41 |
| 8,808,205 B2 * | 8/2014 | Freeman | A61H 31/005 | 601/44 |
| 9,149,412 B2 * | 10/2015 | Faller | A61H 31/006 | |
| 9,180,262 B2 * | 11/2015 | Cota | A61M 16/0875 | |
| 9,603,771 B1 * | 3/2017 | Alvarez | A61H 9/0078 | |
| 11,813,202 B1 * | 11/2023 | McLean | A61G 10/02 | |
| 2002/0174487 A1 * | 11/2002 | Kramer | A61G 7/015 | 5/618 |
| 2003/0178025 A1 * | 9/2003 | Holt | A61H 31/008 | 128/205.13 |
| 2004/0116840 A1 * | 6/2004 | Cantrell | A61M 16/0084 | 601/44 |
| 2005/0085799 A1 | 4/2005 | Luria et al. | | |
| 2006/0118119 A1 * | 6/2006 | Berthon-Jones | A61M 16/06 | 128/206.28 |
| 2007/0045481 A1 * | 3/2007 | Adams | A61G 7/0503 | 248/59 |
| 2008/0078397 A1 * | 4/2008 | Scott | A61M 16/08 | 128/205.25 |
| 2009/0069726 A1 * | 3/2009 | Sherman | A61H 31/00 | 601/44 |
| 2009/0093741 A1 * | 4/2009 | Lach | A61H 31/005 | 601/41 |
| 2009/0133691 A1 * | 5/2009 | Yamada | A61M 11/005 | 128/200.16 |
| 2009/0151073 A1 * | 6/2009 | Kramer | A61G 7/018 | 5/618 |
| 2010/0185127 A1 * | 7/2010 | Nilsson | A61H 31/00 | 601/41 |
| 2010/0324635 A1 * | 12/2010 | Kreck | A61M 16/0479 | 607/105 |
| 2011/0162145 A1 * | 7/2011 | Osborne | G01G 19/445 | 5/613 |
| 2012/0013452 A1 * | 1/2012 | McNeely | G16H 40/63 | 340/286.07 |
| 2012/0102647 A1 * | 5/2012 | Weismiller | A61G 7/0509 | 5/624 |
| 2012/0174319 A1 * | 7/2012 | Menkedick | A61G 7/012 | 5/613 |
| 2014/0024979 A1 * | 1/2014 | Radbourne | A61H 31/006 | 601/41 |
| 2014/0103688 A1 * | 4/2014 | Wilson | A47C 7/46 | 297/284.7 |
| 2014/0323816 A1 * | 10/2014 | Soderberg | A61G 7/0527 | 600/300 |
| 2014/0343466 A1 * | 11/2014 | Herken | A61H 31/008 | 601/41 |
| 2014/0358049 A1 * | 12/2014 | Freeman | A61H 31/005 | 601/43 |
| 2014/0363391 A1 * | 12/2014 | Yannopoulos | A61K 45/06 | 601/41 |
| 2015/0082295 A1 * | 3/2015 | Collins, Jr. | G07C 3/00 | 717/170 |
| 2015/0224005 A1 * | 8/2015 | Kramer | A61G 7/051 | 5/618 |
| 2016/0058639 A1 * | 3/2016 | Lacasse | A61G 7/018 | 5/618 |
| 2016/0338904 A1 | 11/2016 | Lurie et al. | | |
| 2017/0095631 A1 * | 4/2017 | Fukunaga | A61M 16/125 | |
| 2017/0319797 A1 * | 11/2017 | Germinario | A61M 15/0003 | |
| 2018/0133103 A1 | 5/2018 | Lurie | | |
| 2018/0229048 A1 * | 8/2018 | Sikora | A61N 2/002 | |

* cited by examiner

DEVICE FOR CARDIO-PULMONARY RESUSCITATION OF A PATIENT

CROSS REFERENCE TO RELATED APPLICATIONS

This application is the National Stage of PCT/ES2020/070454 filed on Jul. 13, 2020, which claims priority under 35 U.S.C. § 119 of Spanish Application No. U201931210 filed on Jul. 15, 2019, the disclosure of which is incorporated by reference. The international application under PCT article 21 (2) was not published in English.

OBJECT OF THE INVENTION

The present invention relates to a device for practising cardio-pulmonary resuscitation manoeuvres with oxygen therapy on a patient.

The object of the invention is to provide a device for a single attending medical practitioner to practise cardio-pulmonary resuscitation manoeuvres with oxygen therapy, enabling the continuous supply of oxygen to the patient while continuous chest compressions are performed, therefore eliminating the need for a second attending medical practitioner who holds the ventilation mask while the first attending medical practitioner performs interrupted chest compressions.

Advantageously, the device object of the present invention can be used in combination with any existing mechanical or manual continuous ventilation equipment, offering a quick and easy assembly and guaranteeing the correct opening of the patient's airways during resuscitation manoeuvres.

BACKGROUND OF THE INVENTION

Cardiac-respiratory arrest or life-threatening emergency situations for a patient require a quick and effective health intervention because intervention time is a critical variable in the patient survival rate. In this sense, an interruption in pulmonary gas exchange of more than five minutes may cause irreversible damage to some vital organs, particularly brain neurons.

Devices for practising cardio-pulmonary resuscitation manoeuvres on a patient are known in the state of the art, these devices comprising a support base for the cervical region of the patient and a ventilation mask, and usually requiring the cooperation of more than one attending medical practitioner for the proper use thereof.

However, emergency situations in which only one attending medical practitioner is available are commonplace, so devices which require the cooperation of more than one person do not offer the assurance and reliability needed in a life-threatening emergency situation because an effective intervention further requires oxygen therapy, i.e., oxygen supply. Therefore, more than one person must act to guarantee a successful intervention in an emergency situation.

The known devices have a configuration which makes it necessary for at least two or more persons or attending medical practitioners qualified for practising cardio-pulmonary resuscitation manoeuvres to interact with one another. In this sense, one of the attending medical practitioners is exclusively in charge of performing interrupted chest compressions to maintain perfusion and blood circulation to the brain and vital organs, while the other attending medical practitioner is in charge of keeping the airways open, as well as of holding the oxygen supply mask over the patient's face for applying oxygen therapy. Sometimes, even the presence of a third attending medical practitioner is required to use a manual ventilation bag and thereby ensure oxygen therapy.

It should also be pointed out that the placement of known devices is complicated, and this delays the start of the resuscitation manoeuvres, seriously compromising the patient's survival and recovery options. Additionally, devices of this type do not allow a quick release and placement of the patient in a safe position in the event of the patient vomiting during resuscitation operations.

Another drawback of the devices known today lies in the fact that they do not allow a correct hyperextension of the patient's neck based on his/her specific morphological characteristics, so they make it possible to suitably open the airways.

For this reason, the applicant of the present utility model finds the need to offer a device for a single attending medical practitioner to practise cardio-pulmonary resuscitation manoeuvres with oxygen therapy in a safe and efficient manner, said device being simple and easy to place and remove, and adapting to the specific measurements of the patient.

DESCRIPTION OF THE INVENTION

The proposed device solves the problems set forth above in a completely satisfactory manner as it enables a health intervention by a single person, guaranteeing the correct opening of the airways and continuous oxygen supply to the patient without having to interrupt chest compressions.

In this sense, the device for cardio-pulmonary resuscitation of a patient object of the present invention is made up of a support base for supporting a patient, specifically, the shoulders and scapular region of the patient, and a swivel support for supporting the patient's head.

Preferably, the support base is wedge-shaped, which facilitates lifting the patient's chest. Likewise, the support base has guiding means along which complementary guiding means provided in the swivel support run, enabling the swivel support to swivel on the support base. The swivelling of the swivel support therefore facilitates the inclination required to perform a hyperextension of the patient's neck, opening the patient's airways to enable the entry of oxygen.

It should be pointed out that the wedge shape of the support base allows a height difference to be generated between the scapular region of the patient and the horizontal plane, with the patient being positioned on the support base. This height difference allows the swivel support to be swivelled at the angle required for the optimal opening of the patient's airways, and even for the intubation of the patient, if necessary.

The support base further comprises swivel elements connected to at least one pushbutton. This connection is preferably made by means of a flexible polymer spring. Advantageously, the use of polymer materials in the spring prevents its corrosion in environments, such as marine environments, and allows the device to be used in x-ray diagnostic equipment.

The swivel elements of the support base are associated with complementary swivel elements provided in the swivel support, which allows the position of the swivel support to be fixed, preventing the backward movement thereof, and thereby guaranteeing that the patient's neck and head are in the suitable position to facilitate the opening of the airways, and therefore ventilation while practising cardio-pulmonary resuscitation manoeuvres with oxygen therapy.

The pushbutton allows locking and unlocking the swivel elements of the support base and the complementary swivel elements of the swivel support, such that when the pushbutton is actuated, it enables the swivel support to move freely with respect to the support base, by keeping the swivel elements in a shifted position, whereas when the pushbutton is in a standby state, it keeps the swivel elements of the support base coupled to the complementary swivel elements of the swivel support, for fixing the position of the swivel support on the support base.

Therefore, the device offers two different positions: a position in which the swivel support is swivelled, i.e., inclined with respect to the horizontal plane defined by the support base, and a neutral position, in which the swivel support is aligned with the horizontal plane defined by the support base.

Advantageously, the configuration described for the support base and the swivel support allows a correct hyperextension of the patient's neck, with the optimal degree of inclination established in the protocols of medical manuals and guidelines, insofar as it makes it possible to perform this operation based on the specific morphological dimensions of the patient.

The device object of the present invention is complemented with the elements required for coupling and holding a ventilation mask over the patient's face. In this sense, two lateral support elements are connected via attachment means to each of the sides of the swivel support. Advantageously, the attachment means of the lateral support elements make it possible to adapt the device to the specific dimensions of the patient's head. Optionally, the swivel support has notches for receiving the attachment means of the lateral support elements.

The lateral support elements have insertion means for the introduction of a mask holder. Said mask holder is made up of arms provided with a plurality of toothed elements, the arms being attached to a connector with a perforation for coupling a ventilation mask, which is connected to any of the known devices for supplying oxygen. Preferably, the mask holder is made up of a semi-rigid material offering the necessary tolerance so as to make the correct coupling of the mask to the patient's face possible based on the dimensions. This semi-rigid material also makes it possible to adapt the mask holder to the movement of the patient caused by chest compressions, maintaining the fixed position of the mask on the patient's face.

In this sense, the ends of the arms of the mask holder, and therefore the plurality of toothed elements contained therein, are introduced in the insertion means of the lateral support elements, the mask holder being integrally connected to the mentioned lateral support elements. In turn, the insertion means internally have retention means for retaining the plurality of toothed elements of the arms of the mask holder, making it possible to adjust the position thereof vertically based on the dimensions of the patient.

Therefore, with the mask holder, the lateral support elements, and the swivel support being connected, a unit that moves integrally when performing the operation of swivelling the swivel support on the support base is obtained.

Advantageously, in the event of the patient vomiting, any of the lateral support elements can be independently disconnected from the swivel support, an operation which is carried out in a quick and simple manner, releasing the patient so that he/she can be rolled onto his/her side and preventing the risk of the patient aspirating vomit.

When an emergency situation is detected, in order to use the device, the attending medical practitioner places the patient on the support base, resting his/her head on the swivel support. The lateral support elements are then connected to the swivel support, being closely positioned over the patient's face based on the dimensions thereof. If there is an oropharyngeal cannula, said cannula is introduced through the patient's buccal cavity in order to prevent the tongue from obstructing the airways. It should be pointed out that this cannula is not part of the proposed invention. Next, the arms of the mask holder are introduced in the insertion means of the lateral support elements, hermetically coupling the ventilation mask on the patient's face.

Lastly, keeping the pushbutton actuated, the swivel elements of the support base and the complementary swivel elements of the swivel support are unlocked, making it possible for the swivel support to move freely on the guiding means of the support base.

Having performed the hyperextension of the patient's neck, and therefore the opening of the patient's airways, the attending medical practitioner releases the pushbutton, leaving it in the standby position, so the locking means of the support base are connected to the complementary locking means of the swivel support, fixing the position thereof based on the dimensions of the patient and thereby preventing the backward movement of the swivel support.

Once the unit made up of the mask holder, the lateral support elements, and the swivel support is secured and the position thereof is fixed for the hyperextension of the patient's neck, continuous chest compressions are started for cardio-pulmonary resuscitation of the patient, while oxygen is supplied to the patient simultaneously through the mask with any known continuous ventilation device.

Ultimately, the device for cardio-pulmonary resuscitation of a patient object of the present invention allows a single attending medical practitioner to perform an intervention with oxygen therapy and continuous chest compressions, guaranteeing a correct opening of the patient's airways and a quick and effective intervention, thereby increasing the patient survival rate.

BRIEF DESCRIPTION OF THE DRAWINGS

To complete the description that will be made below and for the purpose of helping to better understand the features of the invention, a set of drawings is attached as an integral part of said description in which the following is depicted in an illustrative and non-limiting manner.

PREFERRED EMBODIMENT OF THE INVENTION

Figure 1:
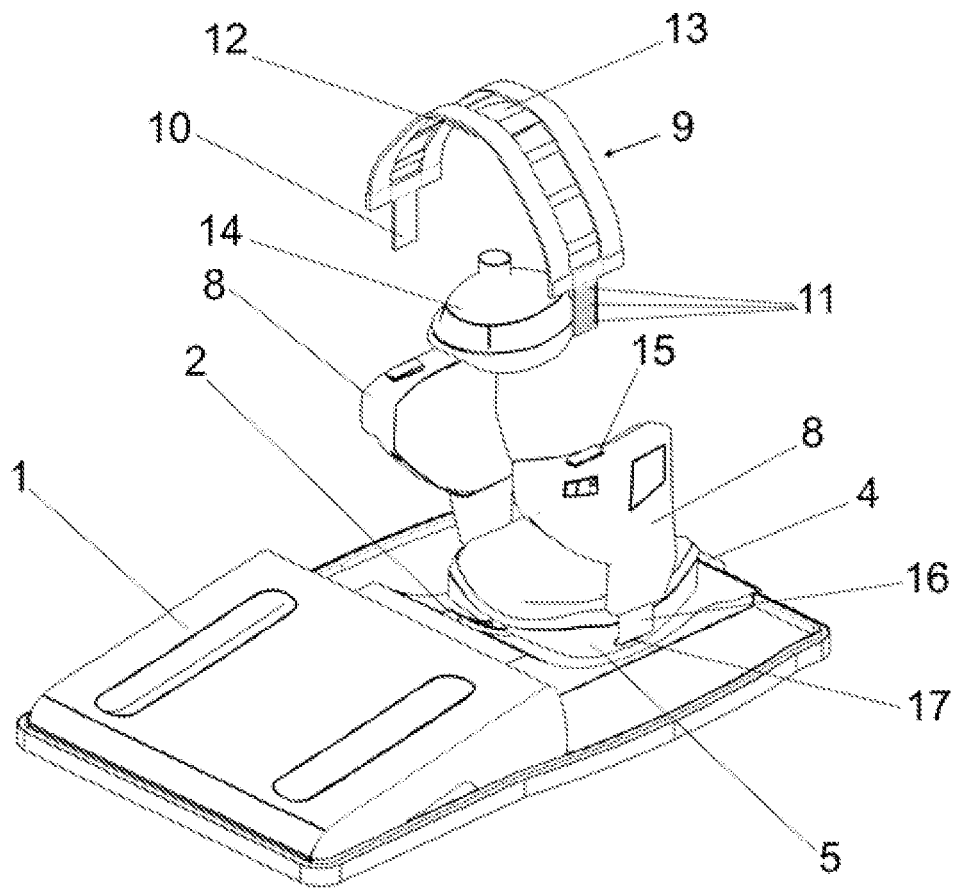
FIG. 1 shows an exploded front view of the device for cardio-pulmonary resuscitation of a patient according to a first embodiment of the invention.

FIGS. 1 to 6 show two preferred embodiments of the invention in detail.

In this sense, it can be seen in the mentioned figures that the device for cardio-pulmonary resuscitation of a patient is made up of a wedge-shaped support base (1), which makes it possible to lift the patient's chest with respect to the horizontal plane, a swivel support (5) for supporting the patient's head, two lateral support elements (8), which are associated with the swivel support (5), and a mask holder (9) which is connected to the lateral support elements (8).

As can be seen in FIGS. 1 to 4, the support base (1) has guiding means (2) along which the complementary guiding means (6) of the swivel support (5) run, making it possible for the swivel support (5) to move such that it swivels on the support base (1). Likewise, the support base (1) comprises swivel elements (3) which are connected to the complementary swivel elements (7) of the swivel support (5) for fixing the position thereof, preventing the backward movement thereof.

The swivel elements (3) of the support base (1) are connected by means of a flexible polymer spring, not depicted in the mentioned figures, to the pushbutton (4) or pushbuttons. The actuation of the pushbutton (4) causes the swivel elements (3) of the support base (1) to shift, thus being disconnected from the complementary swivel elements (7) of the swivel support (5), making it possible for the swivel support (5) to move freely with respect to the support base (1).

This configuration of the support base (1) and the swivel support (5) offers two different positions of the device for cardio-pulmonary resuscitation. Said positions are a first neutral position, shown in detail in FIG. 5, in which the swivel support (5) is aligned with the horizontal plane defined by the support base (1), and a second position, shown in detail in FIG. 6, in which the swivel support (5) is swivelled, offering the required inclination with respect to the horizontal plane defined by the support base (1) to cause the hyperextension of the patient's neck and for opening the patient's airways.

Figure 3:
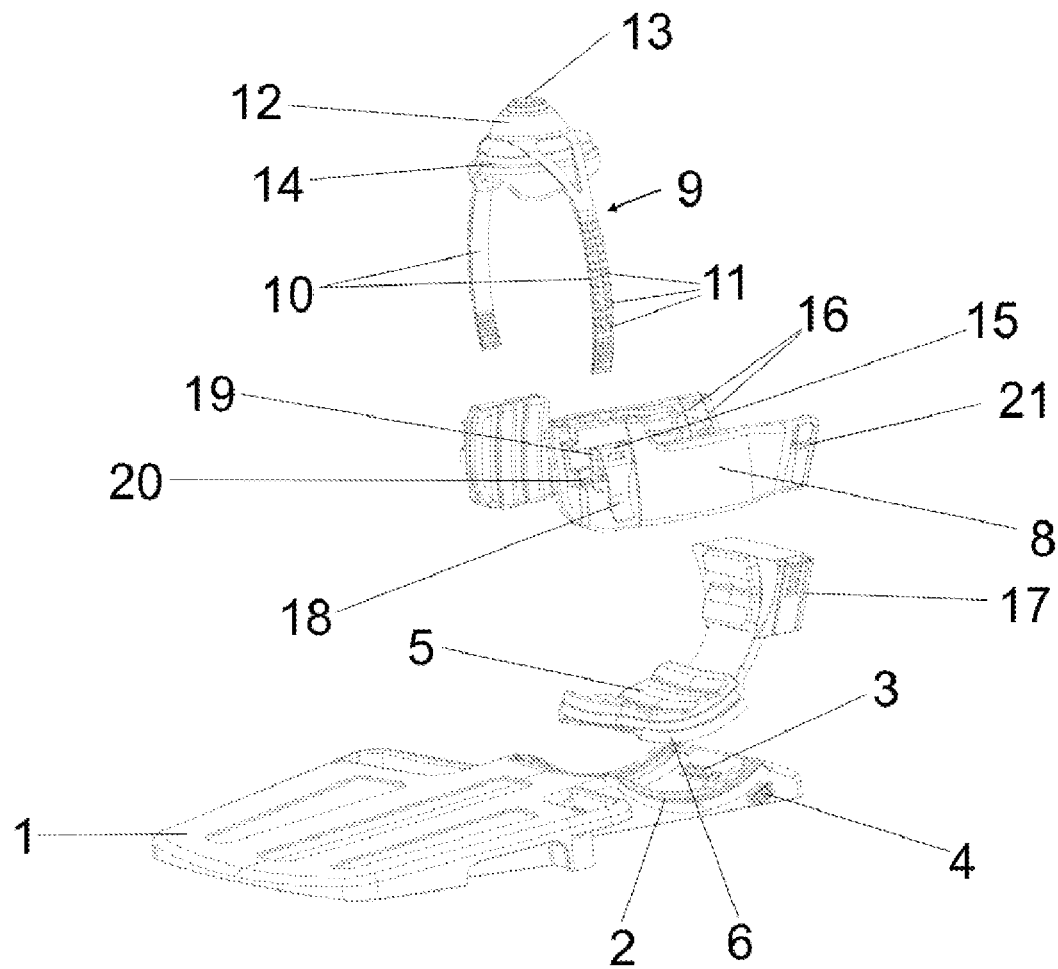
FIG. 3 shows an exploded front view of the device for cardio-pulmonary resuscitation of a patient according to a second embodiment of the invention.
Figure 4:
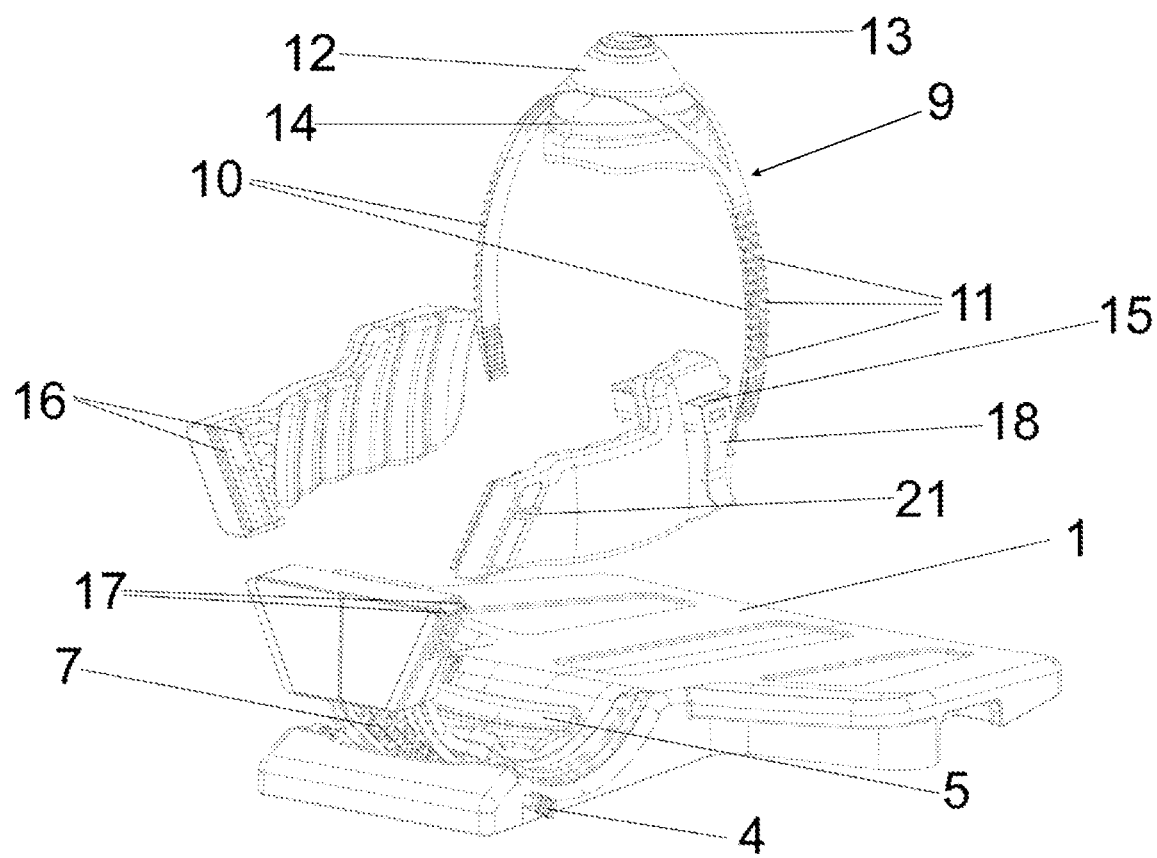
FIG. 4 shows an exploded rear view of the device for cardio-pulmonary resuscitation of a patient according to a second embodiment of the invention.
Figure 5:
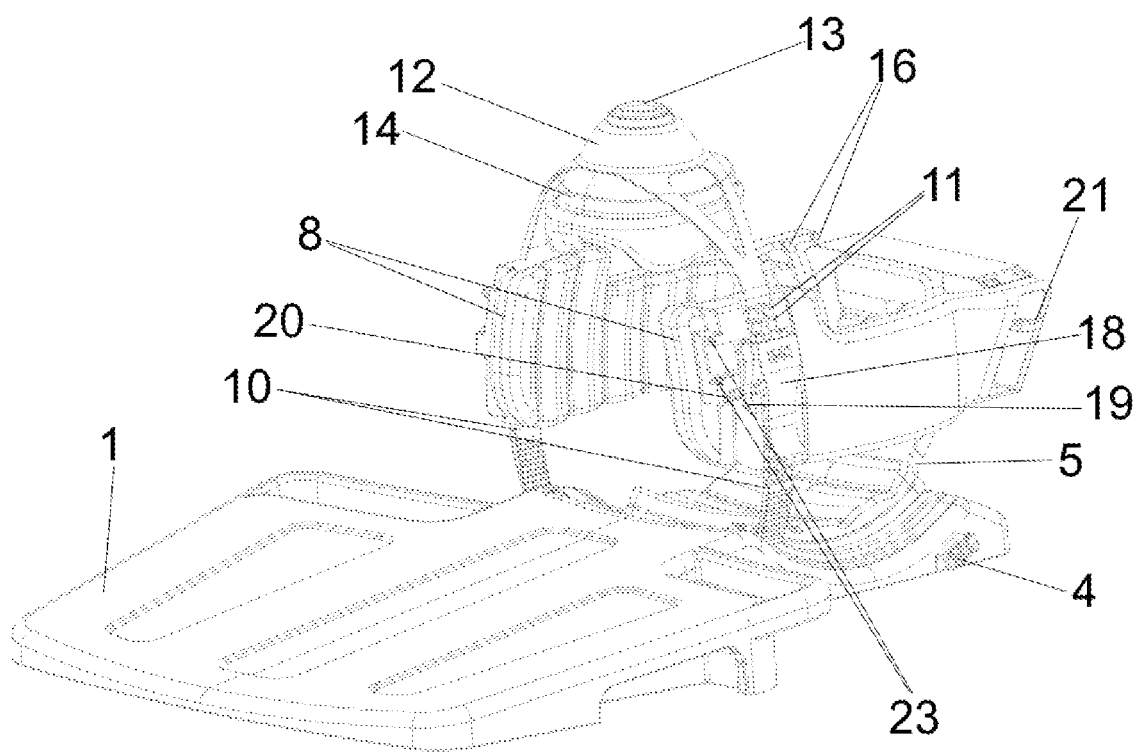
FIG. 5 shows a perspective view of the device assembled and in a neutral position according to a second embodiment of the invention.
Figure 6:
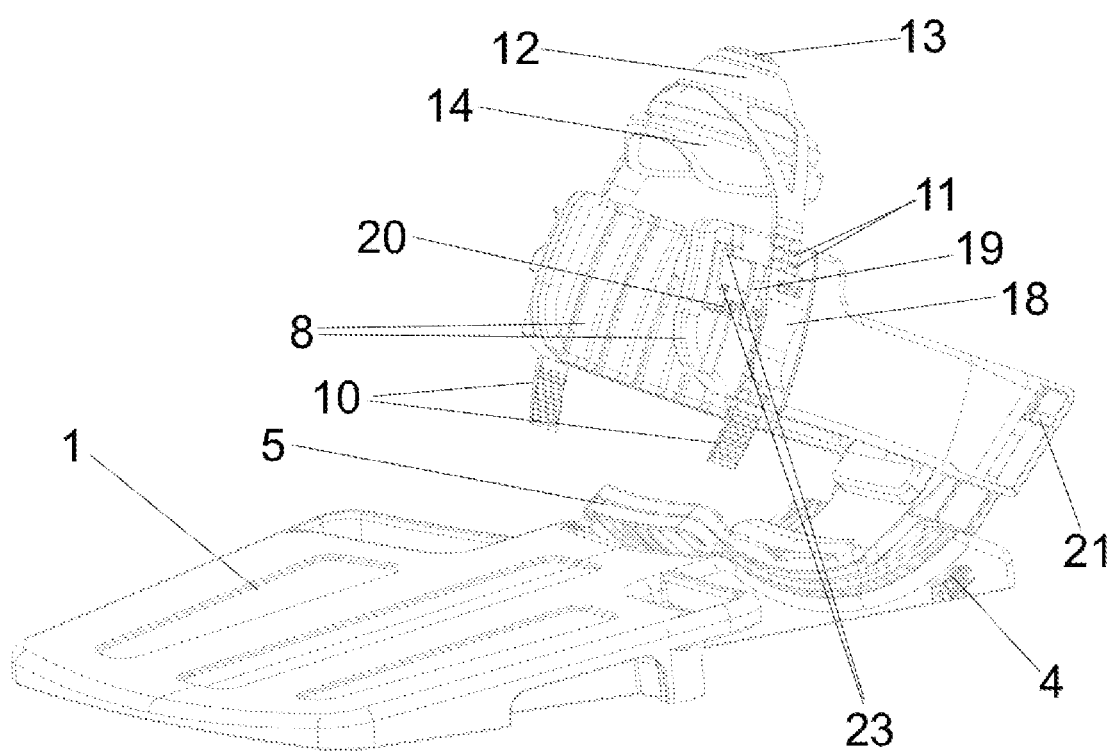
FIG. 6 shows a perspective view of the assembled device once the swivel support has been swivelled for enabling the hyperextension of the patient's neck, according to a second embodiment of the invention.

The device of the invention envisages the incorporation of two lateral support elements (8), with attachment means (16) for the connection thereof to the swivel support (5) through respective notches (17) provided on each of the sides of the swivel support (5), as depicted in FIGS. 1, 3, and 4.

Additionally, the lateral support elements (8) have insertion means (15) for the introduction of the arms (10) of a mask holder (9). The arms (10) are provided with a plurality of toothed elements (11) and attached to a connector (12) with a perforation (13) for coupling a ventilation mask (14). Advantageously, the described mask holder (9) allows the use thereof in combination with any of the known manual and mechanical assisted ventilation equipment and masks.

The ends of the arms (10) of the mask holder (9) are therefore introduced in the insertion means (15) of the lateral support elements (8), the position of the mask holder (9) being vertically adjusted based on the dimensions of the patient. The toothed elements (11) are connected to inner retention means, not depicted in FIGS. 1 to 6, provided in the lateral support elements (8). The mask holder (9) is thereby associated with the lateral support elements (8), and thus with the swivel support (5).

Figure 2:
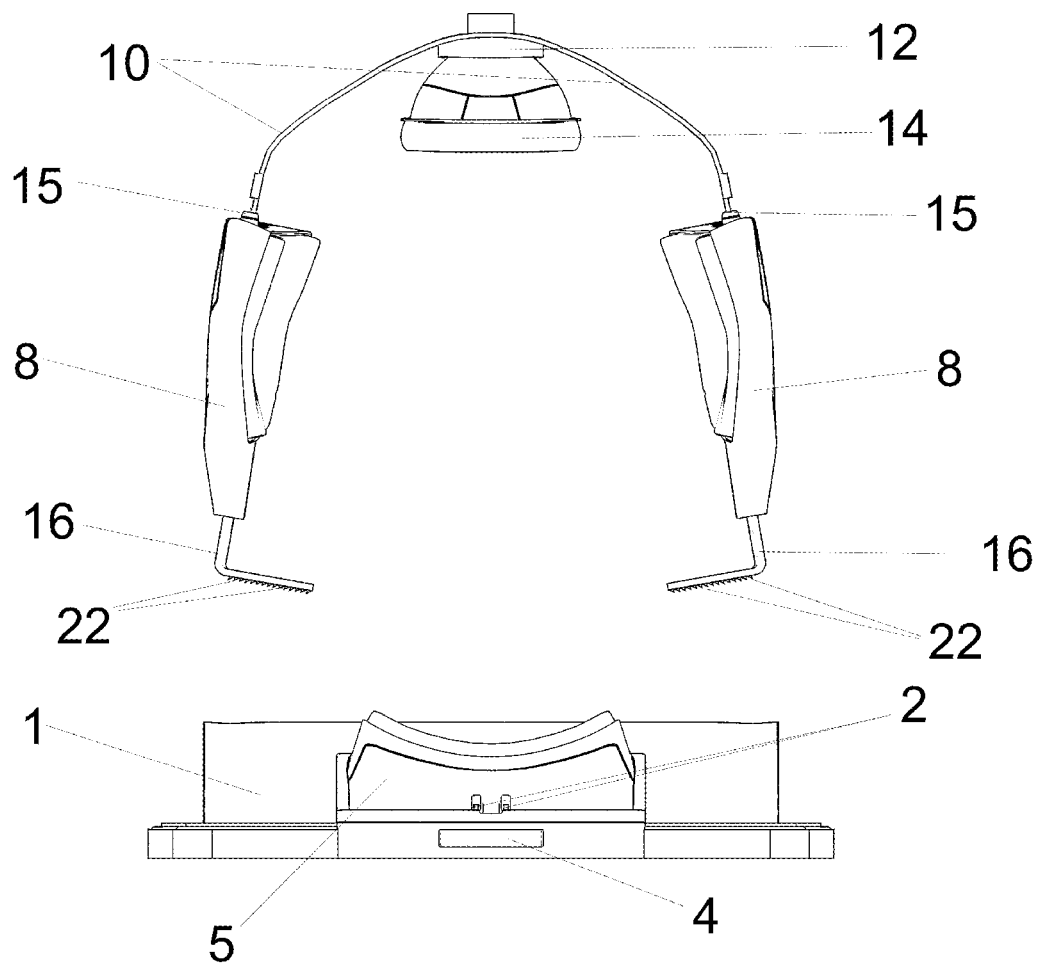
FIG. 2 shows an exploded rear view of the device for cardio-pulmonary resuscitation of a patient according to a first embodiment of the invention.

FIGS. 1 and 2 show a first preferred embodiment according to the present invention. Specifically, FIG. 1 shows a front view of the device in a neutral position, with the lateral support elements (8) coupled in the swivel support (5), whereas FIG. 2 shows a rear view of the device in which the detail of the attachment means (16), prior to the insertion thereof in the notches (17) of the swivel support (5), is seen. As can be seen in FIG. 2, in the illustrated embodiment, the attachment means have a plurality of protrusions (22) which are connected to inner anchoring means (not depicted in the provided figures) of the swivel support (5). Therefore, once the patient has been positioned on the support base (1), the attachment means (16) are inserted in the notches (17) of the swivel support (5) based on the dimensions of the patient, as a result of the presence of the protrusions (22) and the inner anchoring means, with the lateral support elements (8) being perfectly coupled to the patient's face.

FIGS. 3 to 6 show a second preferred embodiment according to the present invention, in which the lateral support elements (8) have horizontal grooves (23) for receiving an adjuster (18) for adjusting the position of the mask holder (9). As depicted in FIGS. 3 and 4, the adjuster (18) offers insertion means (15) for the introduction of the arms (10) of the mask holder (9), as well as locking means (19) for adjusting the position of the mask holder (9) horizontally. Additionally, the lateral support elements (8) have cavities (20) complementary to the locking means (19) for adjusting the mask holder (9) horizontally. Likewise, it can be seen in FIGS. 3 and 4 that, in this second embodiment, the device incorporates a pushbutton (4) on each side, which makes it possible to perform the swivelling operation in a precise and comfortable manner.

Moreover, in the second embodiment illustrated in FIGS. 3 to 6, the swivel support (5) is prolonged until covering the occipital region of the patient's head when the patient is positioned on the device for cardio-pulmonary resuscitation. A portion of the swivel support (5) has a decreasing section in the area coinciding with the occipital region of the patient's head, such that the extent to which the attachment means (16) of the lateral support elements (8) are introduced in the notches (17) of the swivel support (5) is determined by the dimensions of the patient's head, which makes it possible for the lateral support elements (8) to be perfectly adapted to the patient's face based on the dimensions thereof.

In the event of the patient vomiting, to facilitate quickly releasing said patient and rolling him/or onto his/her side, the device envisages the incorporation of release means (21), such as a lever or pushbutton, in each of the lateral support elements (8) for the disconnection thereof from the device, as can be seen in FIGS. 3 to 6.

To achieve a quick and effective placement of the different elements making up the device in a completely symmetrical manner at both ends of the patient's head, the arms (10) of the mask holder (9) have indication means, such as pictograms, areas with a different shade, or alphanumerical codes. Therefore, when the arms (10) of the mask holder (9) are introduced in the lateral support elements (8), it is verified that the vertical adaptation of the mask holder (9) is the same for both arms (10), checking that the indication means of one of the arms (10) corresponds with the indication means of the other arm (10).

Similarly, the lateral support elements (8) have indication means, such as pictograms, areas with a different shade, or alphanumerical codes, which make it possible to verify the correct horizontal positioning of the mask holder (9).

The invention claimed is:
1. A device for cardio-pulmonary resuscitation of a patient, comprising:

a wedge-shaped support base (1) configured for supporting the patient, and being provided with guiding means (2) and swivel elements (3) connected to at least one pushbutton (4), a swivel support (5) configured for supporting the patient's head, and being provided with complementary guiding means (6) and complementary swivel elements (7), a mask holder (9) made up of arms (10) provided with a plurality of toothed elements (11), wherein the mask holder (9) has a connector (12) with a perforation (13) for coupling a ventilation mask (14), at least two lateral support elements (8) having insertion means (15) into which ends of the arms (10) of the mask holder (9) are introduced and inner retention means, and wherein each lateral support element (8) is provided with attachment means (16) for the connection thereof to the swivel support (5), wherein the plurality of toothed elements (11) is introduced in the insertion means (15) of the lateral support elements (8) to enable vertical adjustment of the mask holder (9), and the pushbutton (4), when actuated, allows the swivel support (5) to move freely with respect to the support base (1) by keeping the swivel elements (3) in a shifted position, whereas the pushbutton (4), in a standby state, keeps the swivel elements (3) coupled to the complementary swivel elements (7) for fixing the swivel support (5) on the support base (1) for hyperextension of the patient's neck and for opening the patient's airways.

2. The device for cardio-pulmonary resuscitation of a patient according to claim 1, wherein the swivel support (5) has notches (17) configured for receiving the attachment means (16) of the lateral support elements (8).

3. The device for cardio-pulmonary resuscitation of a patient according to claim 1, wherein the pushbutton (4) is connected to a spring associated with the swivel elements (3) of the support base (1), wherein the spring is made up of a flexible polymer material.

4. The device for cardio-pulmonary resuscitation of a patient according to claim 1, wherein the attachment means (16) have a plurality of protrusions (22) which are connected to inner anchoring means in the swivel support (5) for adapting the lateral support elements (8) to the dimensions of the patient's head.

5. The device for cardio-pulmonary resuscitation of a patient according to claim 1, wherein two adjusters (18) have the insertion means (15) into which the arms (10) of the mask holder (9) are introduced, each adjuster (18) being associated with each of the lateral support elements (8) by means of horizontal grooves (23) provided in the lateral support elements (8), and wherein the adjusters (18) have locking means (19) for adjusting the mask holder (9) horizontally.

6. The device for cardio-pulmonary resuscitation of a patient according to claim 1, wherein a portion of the swivel support (5) has a decreasing cross-section in an area coinciding with an occipital region of the patient's head resting on the swivel support (5).

7. The device for cardio-pulmonary resuscitation of a patient according to claim 1, wherein each lateral support element (8) has release means (21) to disconnect the lateral support element (8) from the swivel support (5).

8. The device for cardio-pulmonary resuscitation of a patient according to claim 1, wherein the arms (10) of the mask holder (9) have indication means for verifying a correct vertical positioning of the mask holder (9).

9. The device for cardio-pulmonary resuscitation of a patient according to claim 1, wherein the lateral support elements (8) have indication means for verifying a correct horizontal positioning of the mask holder (9).

10. The device for cardio-pulmonary resuscitation of a patient according to claim 1, wherein the mask holder (9) is made up of a semi-rigid material.

* * * * *